United States Patent [19]

Poli et al.

[11] Patent Number: 5,445,621
[45] Date of Patent: Aug. 29, 1995

[54] DRUG IDENTIFICATION AND SECURITY APPARATUS FOR INFUSION AND PUMPING SYSTEMS

[75] Inventors: Robert G. Poli, Campbell; Noel L. Johnson, San Jose; Robert R. Burnside; Leland D. Chamness, both of Mountain View; J. Terry Huang, Sunnyvale; V. Stanton Thomas, Palo Alto, all of Calif.

[73] Assignee: Abbott Laboratories, Mountain View, Calif.

[21] Appl. No.: 149,248

[22] Filed: Nov. 9, 1993

Related U.S. Application Data

[63] Continuation-in-part of Ser. No. 811,516, Dec. 20, 1991, abandoned.

[51] Int. Cl.⁶ .............................................. A61M 5/00
[52] U.S. Cl. ..................................................... 604/246
[58] Field of Search ................... 604/67, 83, 110, 131, 604/151-155, 246; 128/DIG. 12

[56] References Cited

U.S. PATENT DOCUMENTS

| | | | |
|---|---|---|---|
| 4,565,542 | 1/1986 | Berg | 604/131 |
| 4,627,839 | 12/1986 | Young | 604/121 |
| 4,842,584 | 6/1989 | Pastrone | 604/50 |
| 4,865,584 | 9/1989 | Epstein et al. | 604/67 |
| 4,978,335 | 12/1990 | Arthur, III | 604/67 |
| 5,006,050 | 4/1991 | Cooke et al. | 604/153 |
| 5,009,641 | 4/1991 | Gorton | 604/131 |
| 5,078,683 | 1/1992 | Sancoff et al. | 604/67 |
| 5,153,827 | 10/1992 | Coutré et al. | 604/67 |

Primary Examiner—C. Fred Rosenbaum
Assistant Examiner—Manuel Mendez
Attorney, Agent, or Firm—Harry G. Thibault; Thomas M. Breininger

[57] ABSTRACT

A drug identification and security apparatus usable in conjunction with an electronic drug delivery system having at least one drug channel therein, the apparatus providing a first interlock mechanism between a locking member of the apparatus and the drug delivery system to lock the upper and lower doors of the drug channel and to disengage the drug delivery system and prevent removal of a drug container/cassette assembly when the locking member is in a locked position. A second interlock mechanism is interposed between a bar code reading device usable with the drug delivery apparatus and a sensor provided on the drug delivery system, the sensor assuring the placement of a cassette assembly in a drug channel with a scanner activating a switch to enable the scanner to read identifying indicia provided on a drug container of a cassette assembly installed in the drug channel, and both cassette sensor and scanner switch must be activated to enable a scan of a drug container installed in the drug channel, to enable the drug delivery system to deliver the drug in the container through the drug channel to the patient receiving a drug dosage in a controlled amount and at a controlled delivery rate.

30 Claims, 11 Drawing Sheets

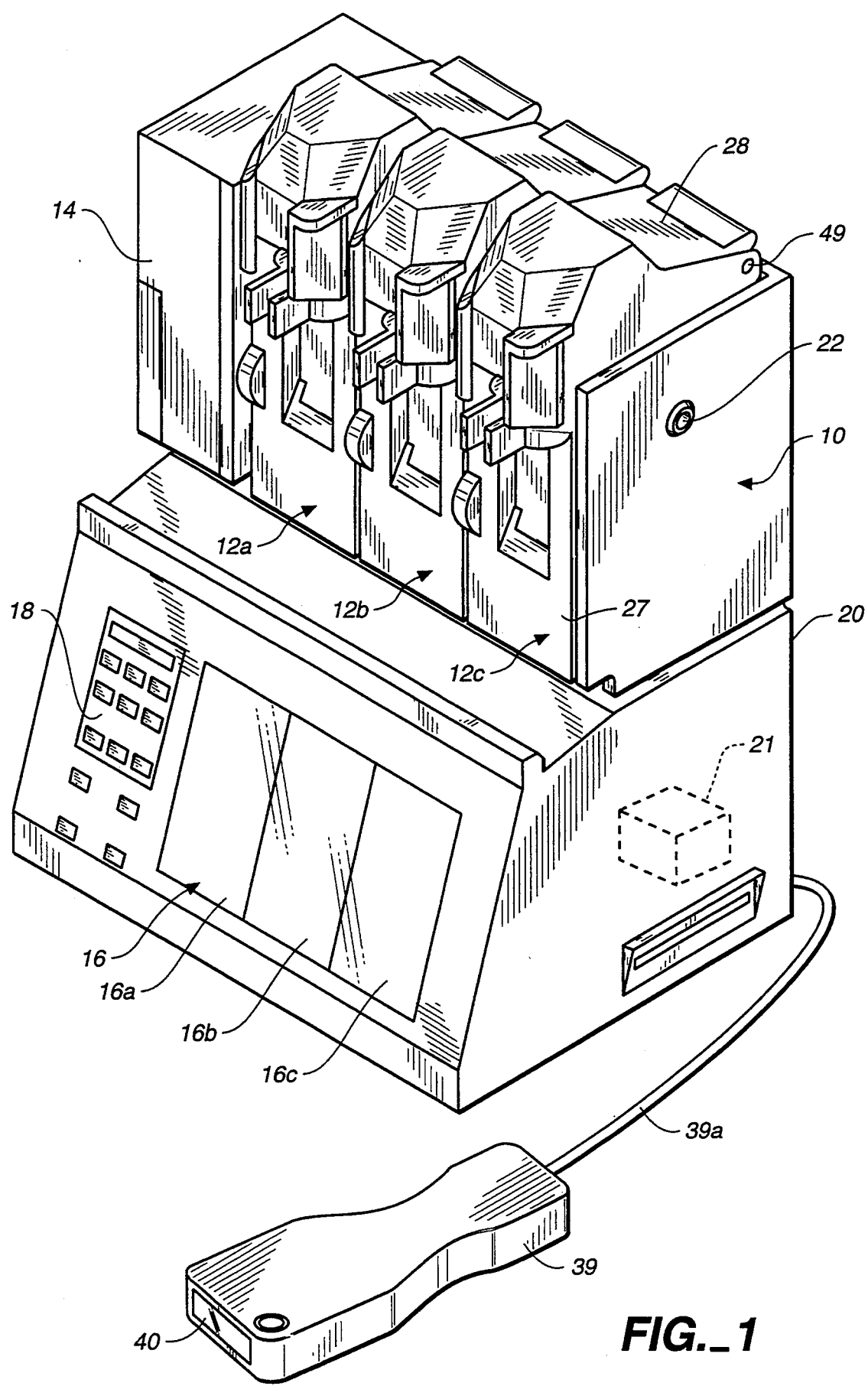
FIG._1

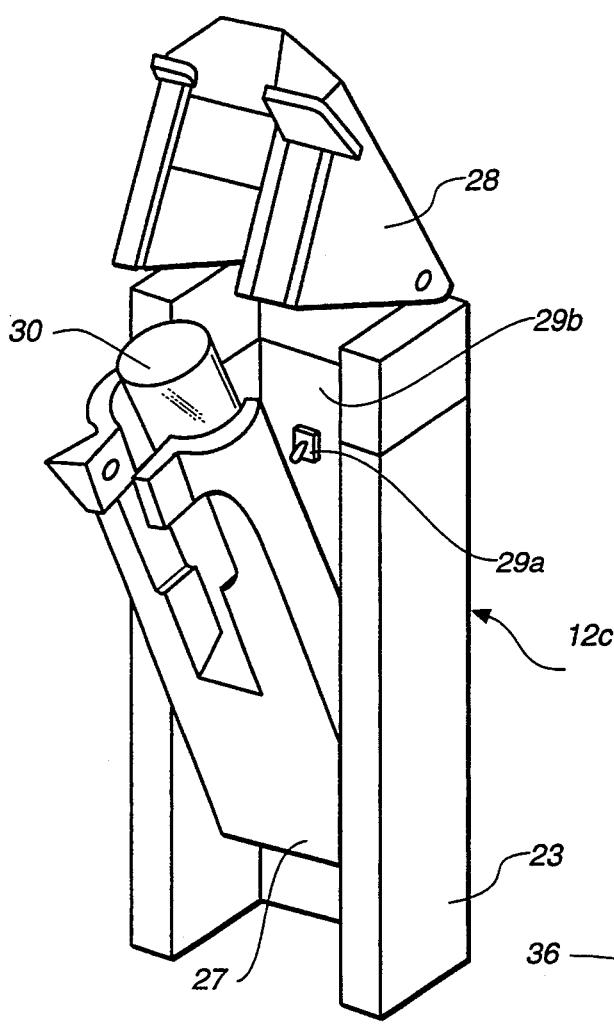
FIG._2
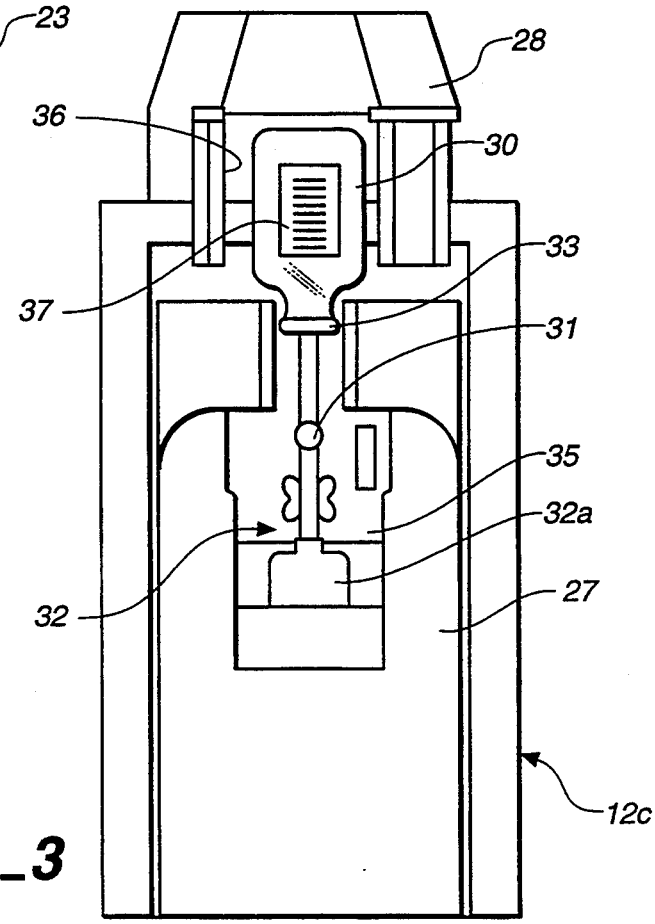
FIG._3

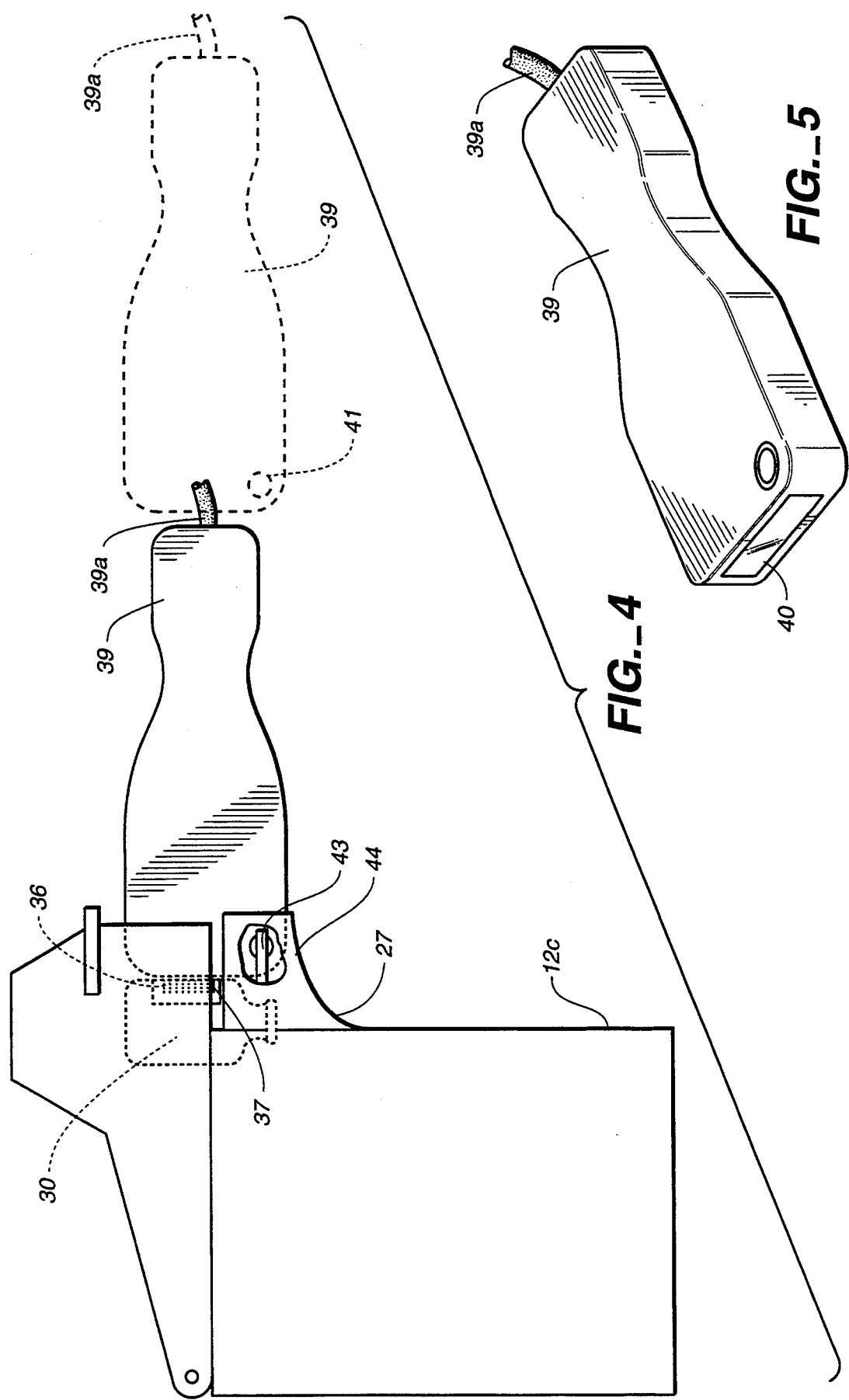

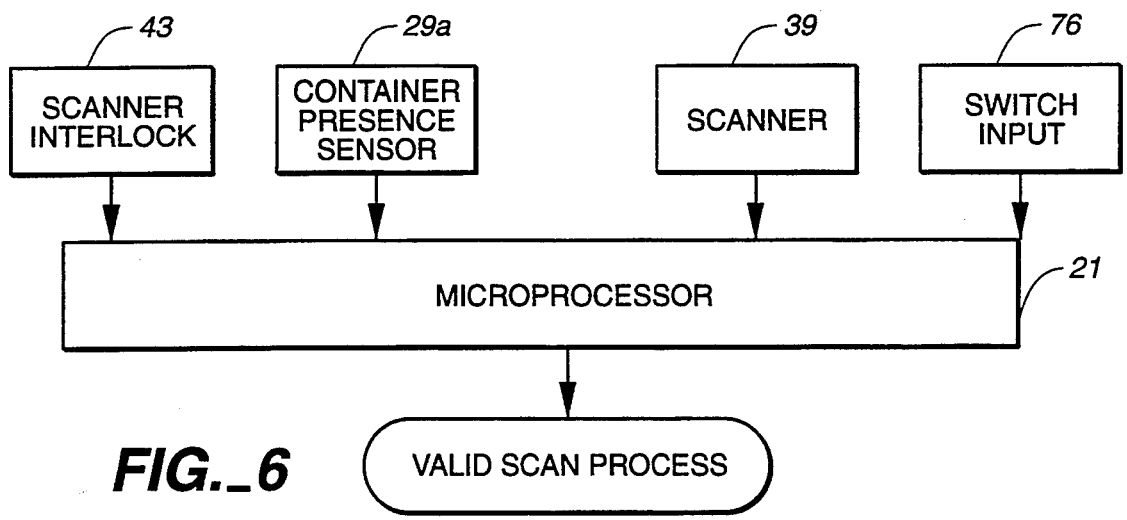
*FIG._6*
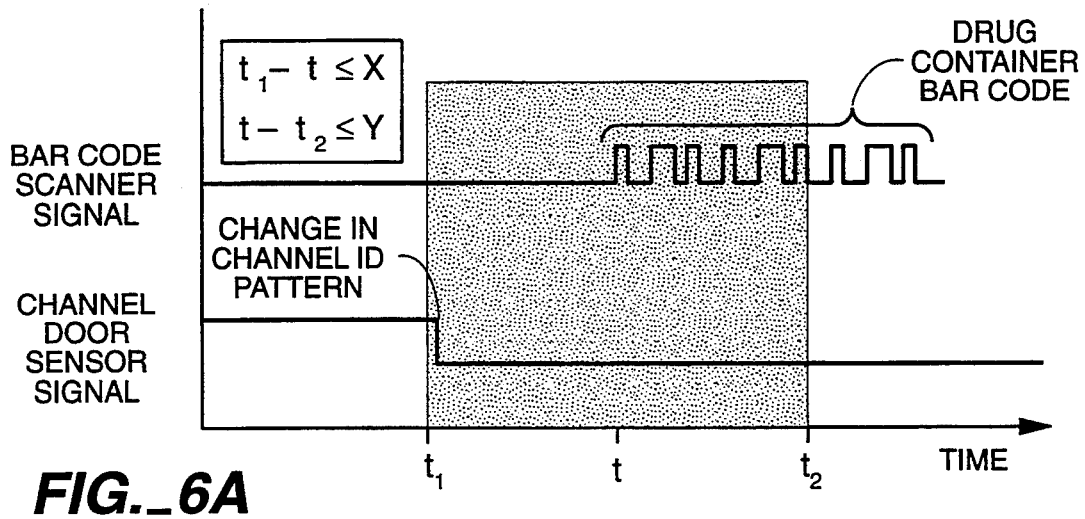
*FIG._6A*
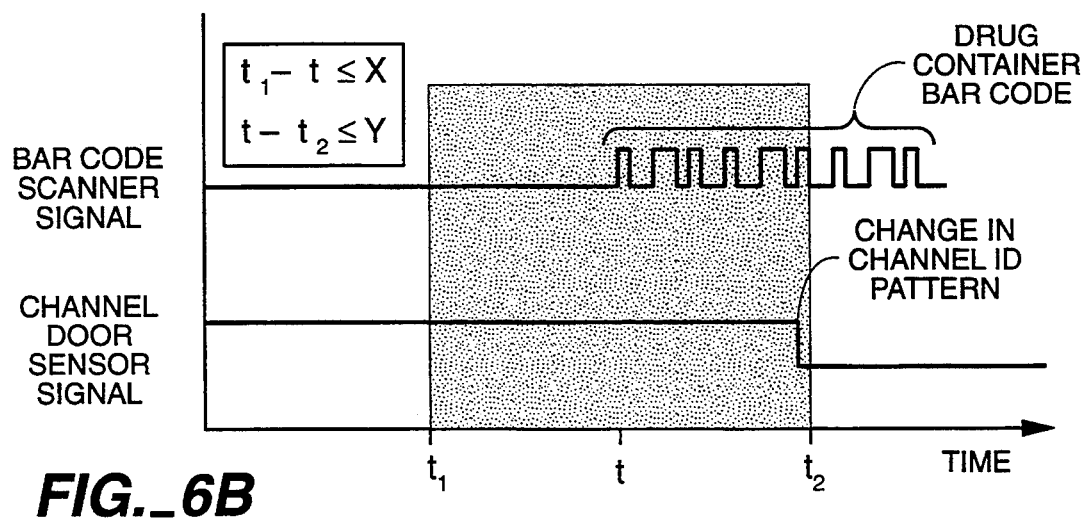
*FIG._6B*

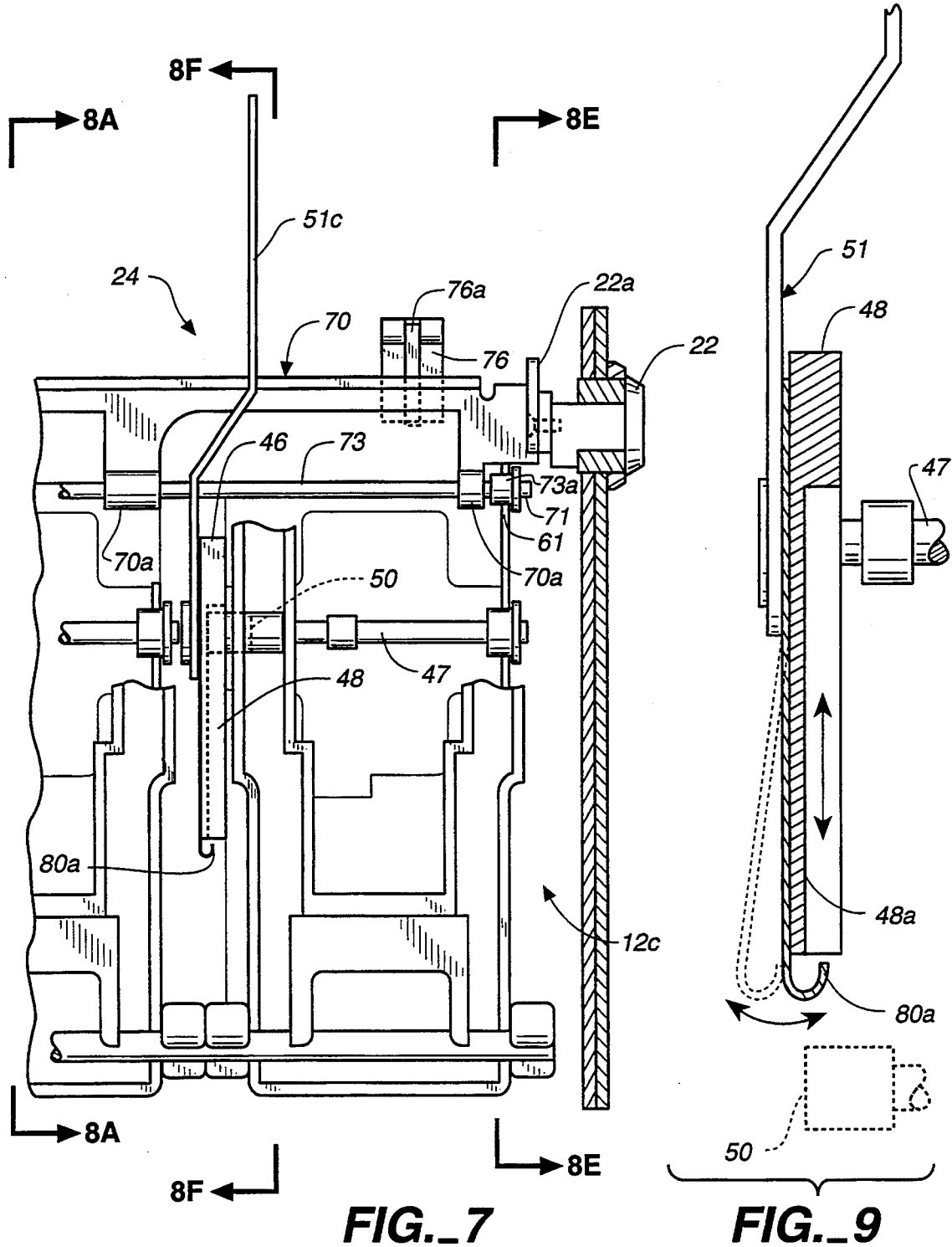
FIG._7  FIG._9

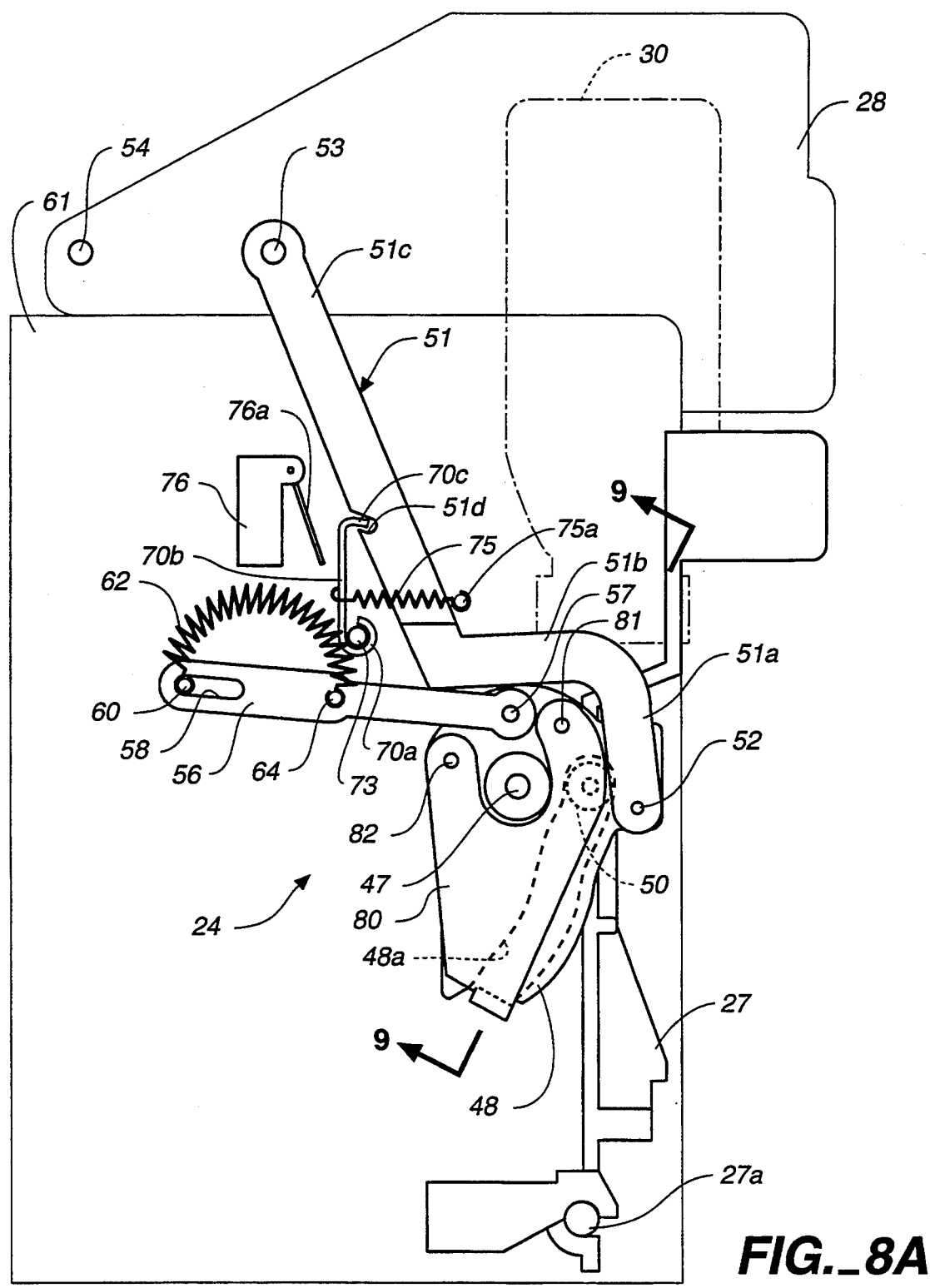
FIG._8A

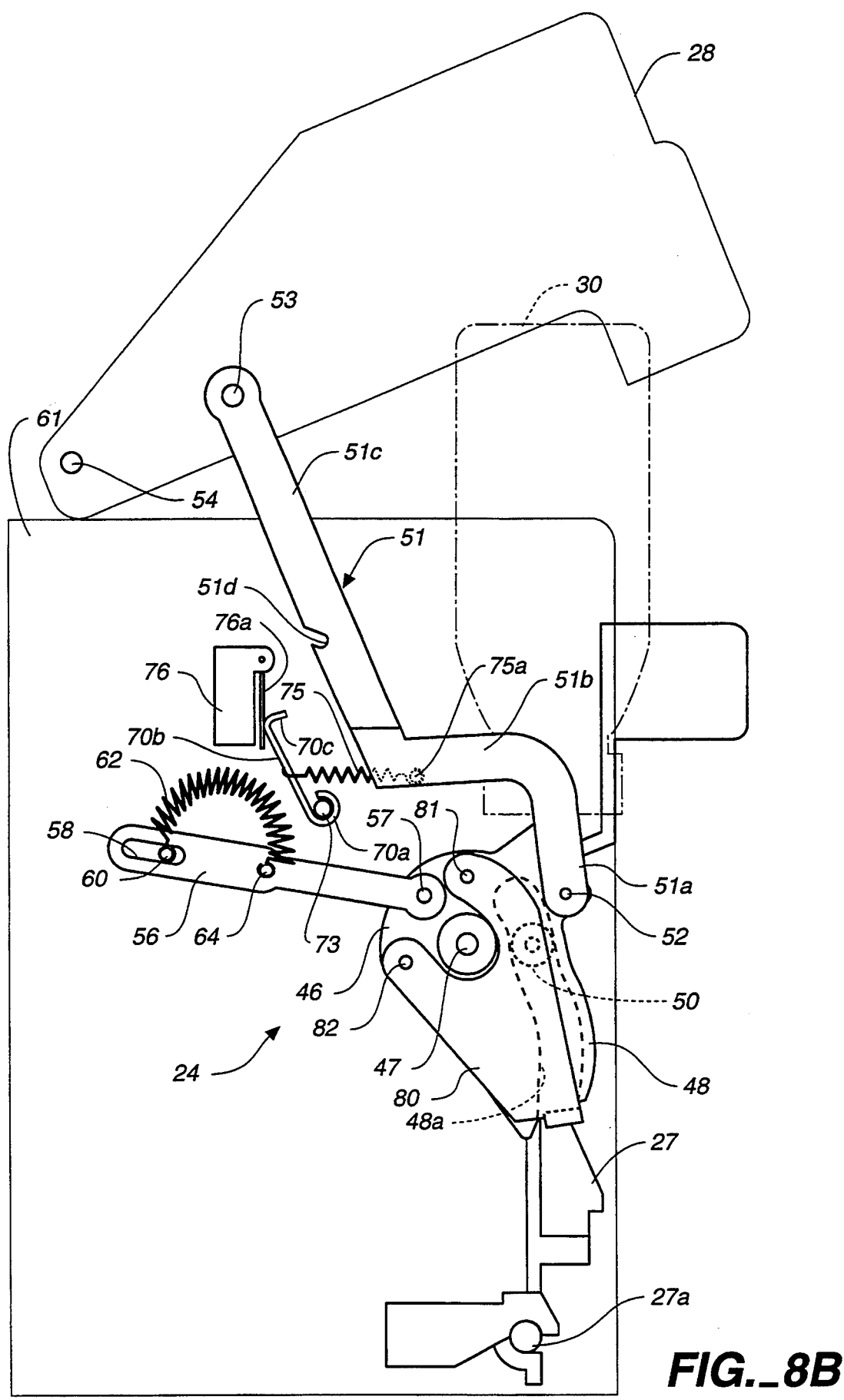
FIG._8B

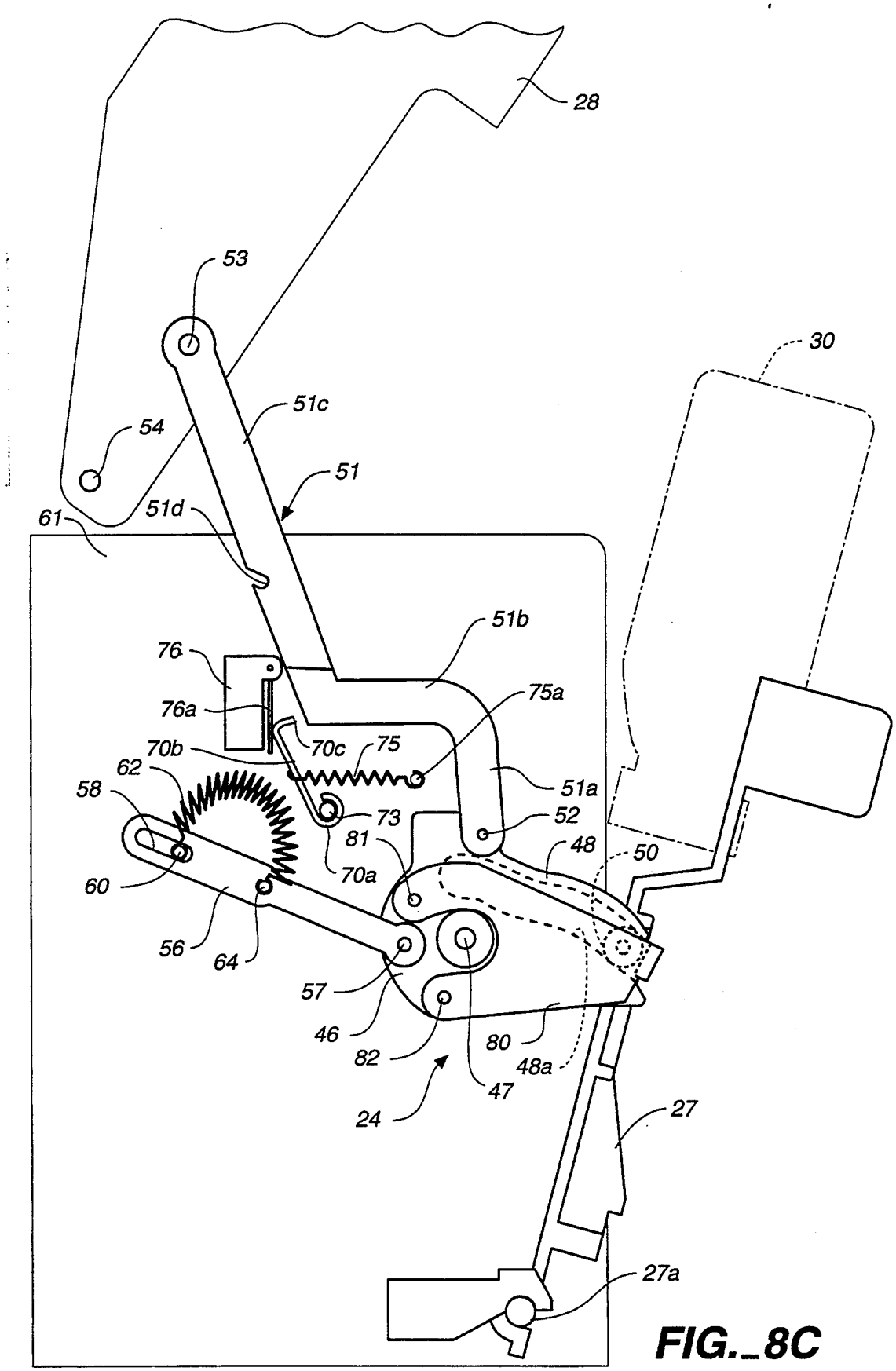
FIG._8C

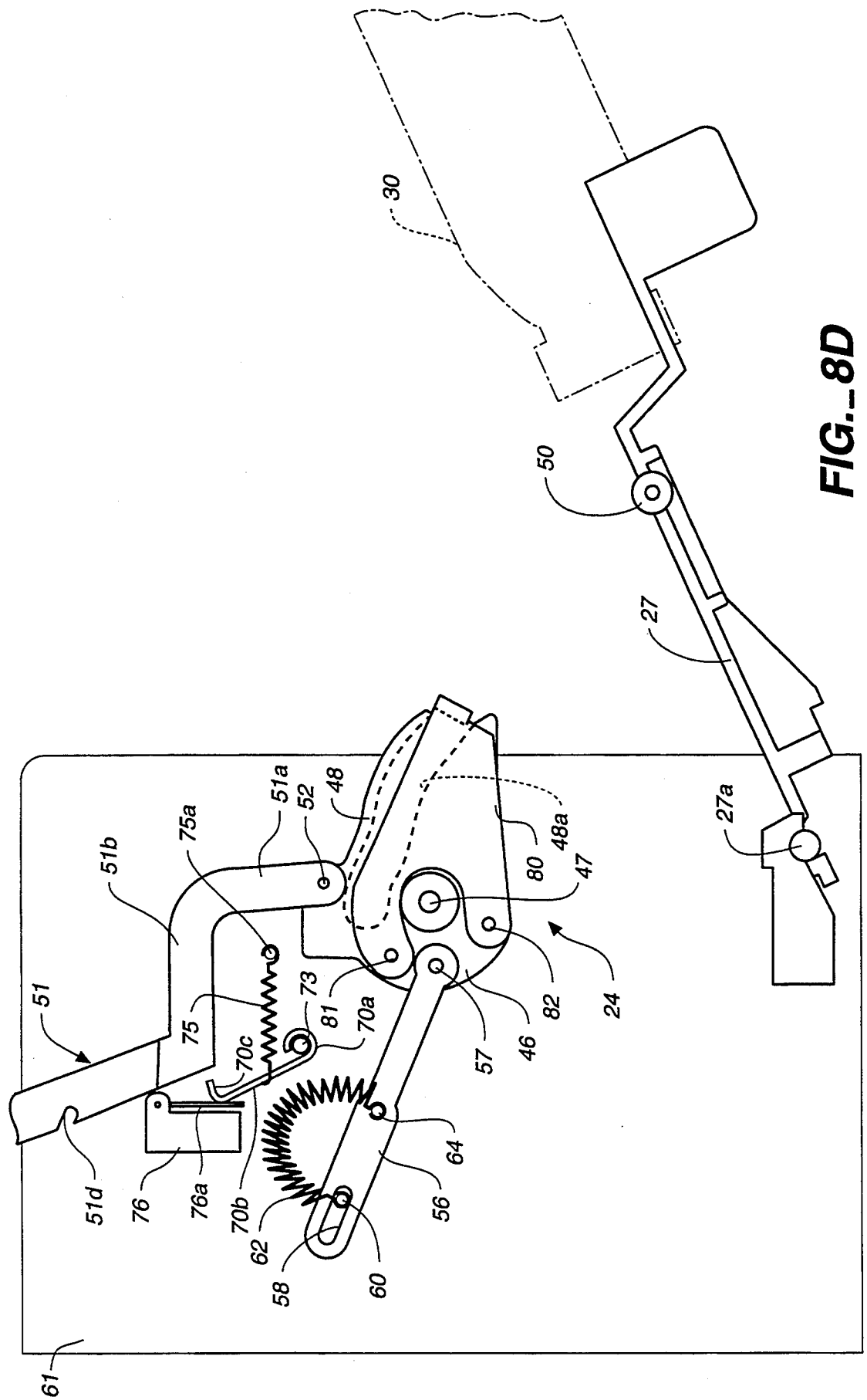
FIG._8D

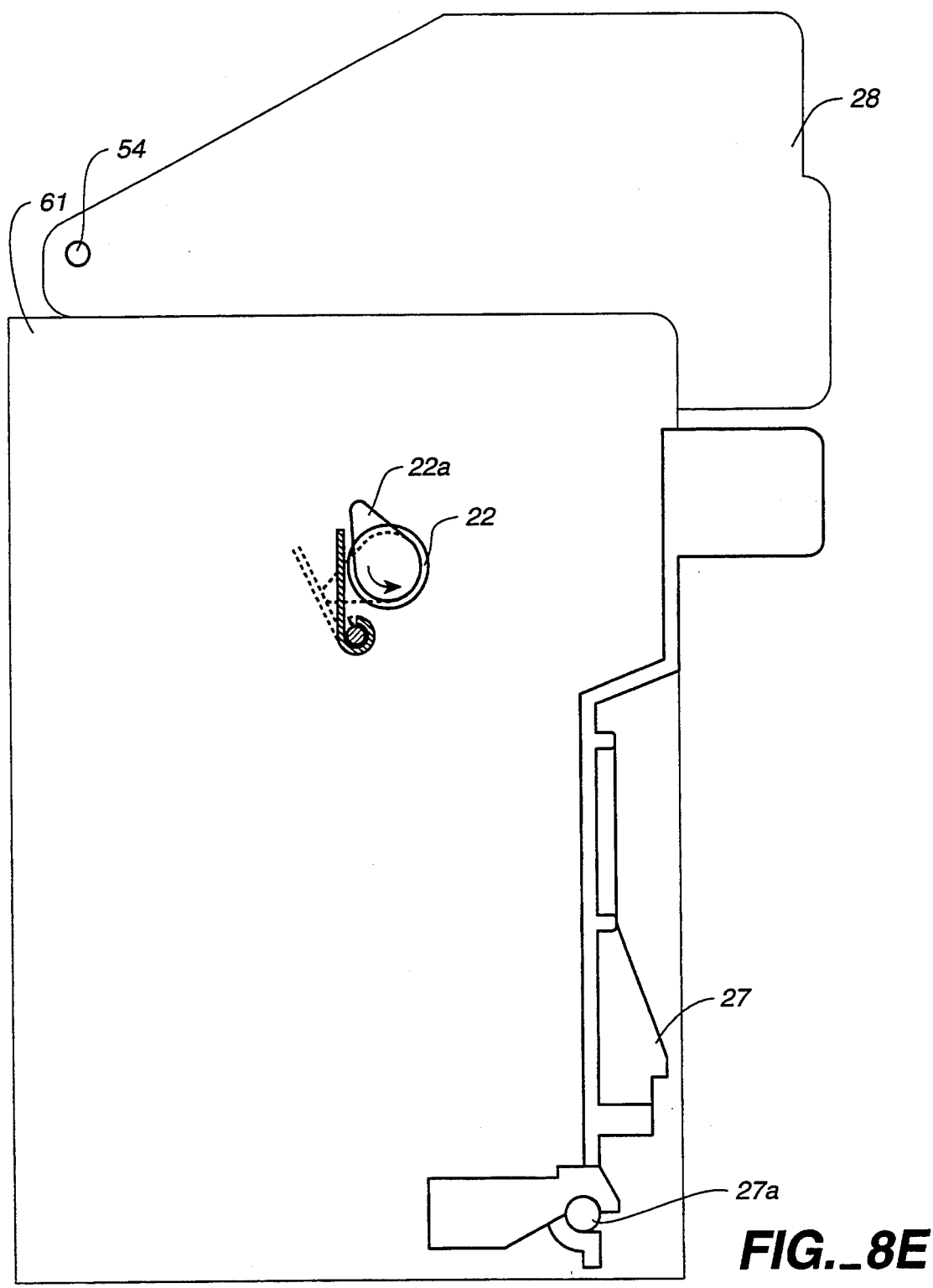
FIG._8E

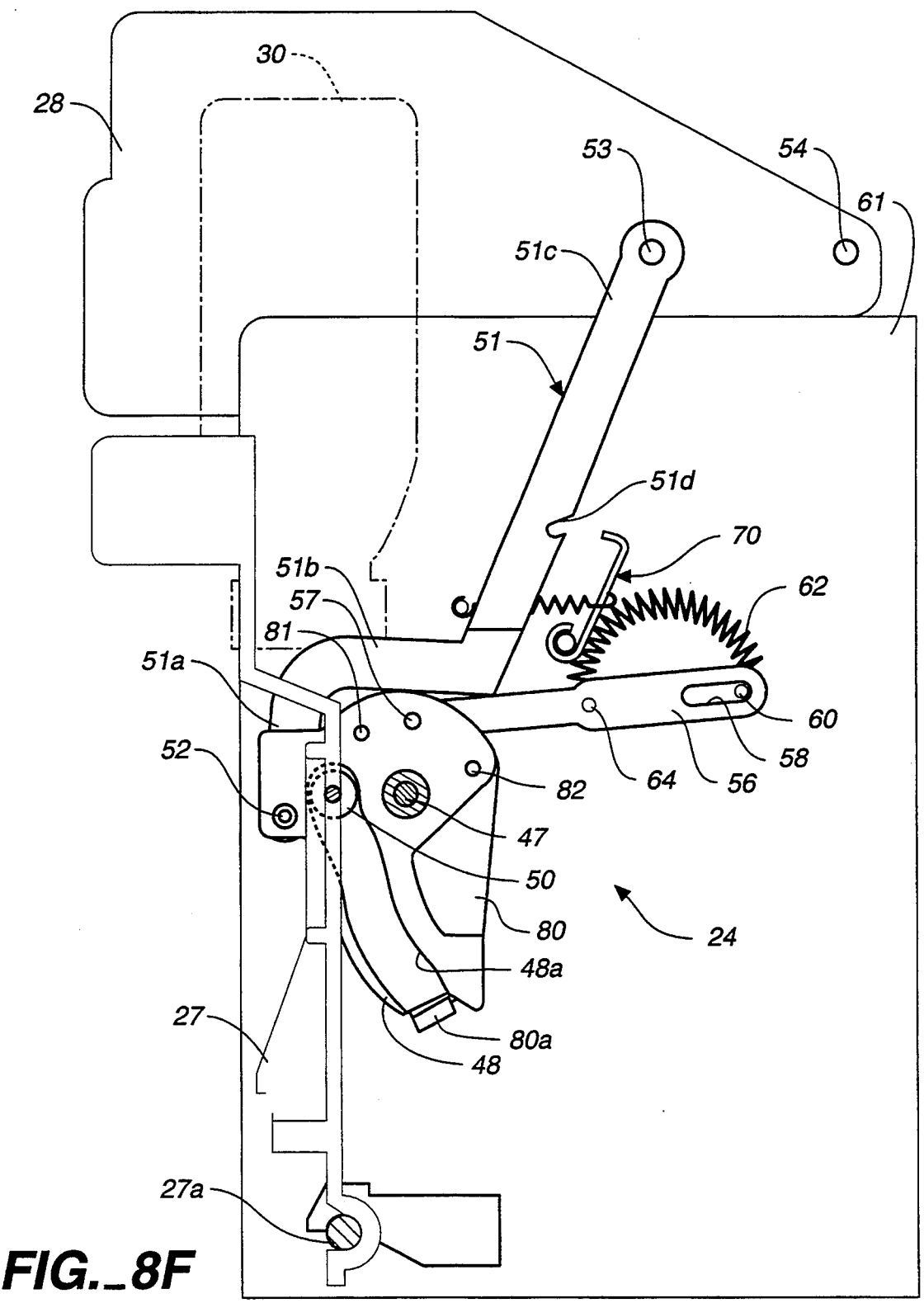
FIG._8F

DRUG IDENTIFICATION AND SECURITY APPARATUS FOR INFUSION AND PUMPING SYSTEMS

RELATED APPLICATIONS

This document is a continuation-in-part of prior U S. patent application Ser. No. 811,516 filed on Dec. 20, 1991, (now abandoned). The benefit of the filing date of the prior application is hereby claimed under 35 U.S.C. § 120.

FIELD OF THE INVENTION

The present invention relates to drug identification and security apparatus generally and in particular to a drug channel drug identification and security apparatus useful in a drug delivery system to prevent the dispensing of drugs when the system is locked and further to assure that the drug container from which the drug is dispensed is disposed in the drug delivery system.

BACKGROUND OF THE INVENTION

It is known to provide a locking enclosure for a drug delivery device such as a programmable infusion pump to permit the pump to be used as a patient-controlled analgesia (PCA) device. For example, depicted in U.S. Pat. No. 4,627,839 entitled "Patient Controlled Analgesia Conversion", is a pump which infuses a drug into the patient at a dosage set by the doctor but at a rate controlled by the patient. To prevent the patient from accessing the pump to obtain more drug than prescribed, safety interlocks are provided to disable the keyboard once dosage requirements have been set and the pump is operative. However, under certain circumstances it might be necessary to disable the mechanism itself, as in a drug delivery situation where the physician needs to be present during the time of drug delivery and needs to prevent the delivery of drugs in his absence. An accommodation as described above is not available in the aforementioned device. Another form of locking member associated with a patient controlled analgesia device is shown in U.S. Pat. No. 5,009,641 entitled "Patient-Controlled Analgesia Security Attachment For A Medication Infusion System". The subject patent discloses both a compartment for securely storing a medication supply and means for preventing either a cassette associated therewith or a fluid line between a storage compartment and a cassette from being removed or tampered with. However, such an attachment offers no advantage to the programming of multiple infusion devices and further does not permit the disablement of such devices subsequent to programming and prior to use so as to prevent unauthorized activation of the device when the physician programming the device is not present.

While it may be possible to provide within a single drug delivery apparatus a bar code reader fixedly mounted on the device, such as shown in U.S. Pat. No. 4,978,335 entitled "Infusion Pump Of Bar Code Input To Computer", such a scheme is not suitable for all drug delivery applications. For example, a hand-held reader may be preferable to a built-in reader for certain applications. In such applications it would be desirable to know that the vial being read is properly installed inside the device. Further, such consideration would also apply to a multi-channel drug delivery apparatus using but a single hand-held bar code reader.

Accordingly, in a drug delivery system having multiple drug channels which uses a single bar code reader, it may be necessary to provide a bar code reader which is hand-held and moveable to scan each drug channel of the system and further to provide a drug identification and security apparatus with interlock means to assure that a drug container is disposed within its respective drug delivery channel of the drug delivery system and further means to assure that the bar code scanner reads the bar code on the drug container installed within its respective drug delivery channel in the drug delivery system. Moreover, in such a proposed apparatus it is clearly necessary that the apparatus prevent the scanner from reading the bar code of a drug container not installed in the apparatus or a drug container not properly positioned for reading within the drug delivery system.

SUMMARY OF THE INVENTION

In accordance with the present invention, a multi-channel drug delivery system includes a drug identification and security apparatus to insure proper placement of a drug container within a discrete channel of the system, and further to provide that a simple turn of a key will electronically disengage the system to prevent its operation in the absence of the physician attending the system, as well as to prevent the removal of the drug container.

In particular, the proposed drug identification and security apparatus provides a first interlock to ensure that a drug container installed in a preferred embodiment of the drug delivery system is properly installed within a drug delivery channel of the system for reading by a scanner device. A second interlock maintains the system in a closed configuration once the drug container has been installed in the system and further electronically inactivates the system to insure that the drug contained in the container installed therein cannot be dispensed in the absence of the attending physician.

In accordance with the present invention, a drug identification and security apparatus is usable in conjunction with an electronic drug delivery system, the drug delivery system comprising a multi-channel device wherein each drug delivery channel includes a pump mechanism, a pump cassette installed in the mechanism, a drug container connected to the cassette via a container adapter, and a drug channel enclosure enclosing each drug delivery channel of the device. The drug identification and security apparatus includes a locking member in engagement with the drug channel and movable between separable lock and unlock positions. A position sensor interposed between the locking member and the drug delivery system electronically disengages said system when the locking member is in the lock position.

Provided in association therewith is a drug identification apparatus which includes a scanning device for reading identifying indicia, such as a bar code, provided on the drug container. An interlock mechanism includes means interposed between the scanning device and the drug channel enclosure to assure the presence of the drug container in a drug channel of the enclosure at a designated position within such enclosure, to enable the drug delivery system to activate a drug container scan, to identify the drug in the drug channel, to permit the entry of selected drug parameters, to deliver the drug in the container through the system to a patient receiving a drug dosage in a controlled amount and at a controlled delivery rate as specified.

The proposed drug identification and security apparatus offers multiple levels of protection to the user of the automated electronic drug delivery system used in conjunction with the present invention. First the proposed drug identification interlock assures that the drug container is placed within the system before use and that the apparatus is identifying the drug container placed in the system and not a drug container disposed remotely from the apparatus. In a multi-channel drug delivery system the drug identification and security apparatus can identify drug containers disposed in respective drug channels and enable the user to program a drug channel once its drug container has been installed therein and identified by an appropriate scanning device.

Moreover, once a drug container has been installed in its respective drug delivery channel and the channel has been programmed per the requirements of the attending physician, the drug identification and security apparatus provides additional security to the attending physician by first locking the drug container within the drug delivery system, and second, providing means to electronically disable that drug delivery system in the absence of the attending physician.

Further objects and advantages of the present invention will become apparent upon a reading of the detailed description of the preferred embodiment as set forth below, particularly when such detailed description is considered in conjunction with the accompanying drawings briefly described below.

BRIEF DESCRIPTION OF THE DRAWINGS

FIG. 1 is a top right perspective view of a multi-channel electronic drug delivery system which employs the drug identification and security apparatus of the present invention;

FIG. 2 is a top right perspective view of the right-hand drug channel of FIG. 1, with a protective hood enclosure open, to expose the drug vial therein;

FIG. 3 is a front elevation of the drug channel of FIG. 2, having a drug vial disposed therein;

FIG. 4 is a side elevation of the drug channel of FIG. 2, showing the alignment of the drug channel with a bar code scanner;

FIG. 5 is a perspective view of the bar code scanner of FIG. 4;

FIG. 6 is a block diagram showing the interaction of a drug channel interlock with the microprocessor;

FIGS. 6a and 6b are timing diagrams plotting both the bar code scanner signal and the channel door sensor signal versus time;

FIG. 7 is a front elevational view of the drug channel of FIG. 2 with the cover and certain other portions of said channel removed for clarity;

FIG. 8a is a view taken generally along lines 8a—8a of FIG. 7 with a cassette assembly including the drug container in place in the drug channel and both the lower door and the hood fully closed;

FIG. 8b is a view similar to FIG. 8a with the hood partially raised;

FIG. 8c is a view similar to FIG. 8a with the hood fully raised and the lower door open;

FIG. 8d is a view similar to FIG. 8a in which the hood is removed and a spring release enables the lower door to fully rotate about a lower pivot point;

FIG. 8e is a view taken generally along the lines 8e—8e of FIG. 7;

FIG. 8f is a view taken generally along the lines 8f—8f of FIG. 7; and

FIG. 9 is a view taken along lines 9—9 of FIG. 8a.

DETAILED DESCRIPTION OF THE PREFERRED EMBODIMENT

Shown in FIG. 1 is a multi-channel electronic drug delivery system 10. Such system includes three substantially equivalent drug delivery channels 12a, 12b, and 12c. The system also includes a fluid delivery channel 14 adjacent the drug delivery channels. Drug delivery parameters are displayed on a touch screen 16. Drug delivery parameters are entered via a touch screen segment 16a, 16b, or 16c for respective drug channels 12a, 12b, or 12c, and fluid delivery parameters for fluid channel 14 are entered via a key pad 18. A base enclosure 20 of the electronic drug delivery system 10 encloses a host computer 21 (FIG. 6) for driving the system 10. Key lock 22 is disposed on one side of the drug channel 12c and engages a security interlock 24 (FIGS. 7,8) discussed in detail below. A bar code reader 39 is electronically connected to the system 10 as by a cord 39a.

The right hand drug delivery channel 12c is in the perspective view of FIG. 1. Single drug delivery channel 12c is discussed in detail since the drug delivery channels 12a, 12b, and 12c are identical.

Referring now to FIGS. 2 and 3, it should be noted that the drug delivery channel 12c includes a drug delivery system similar to that described in U.S. Pat. No. 4,842,584 entitled Disposable Fluid Infusion Pumping Chamber Cassette and Drive Mechanism thereof, issued Jun. 27, 1989, to the assignee of the subject application. To enable the reader to fully understand the structure of the drug infusion pump associated with the drug delivery channel of the present invention, such U.S. Patent is herein incorporated by reference.

As best seen in FIGS. 2 and 3, the drug delivery channel 12c includes an enclosure member 23 including a pivotable lower door 27 operable in conjunction with a pivotable hood 28. As best seen in FIGS. 8a—8e, the lower door 27 pivots around pivot point 27a to permit a cassette assembly 32 to be inserted into the drug channel 12c.

When the door 27 pivots to a closed position as shown in FIG. 3, the cassette assembly 32 is disposed in active position therein. The cassette assembly 32 comprises a cassette 32a connected to a container adapter 31, which is then connected to a drug container 30 of the cassette assembly 32 through a container cover 33. The upper enclosure or hood 28 overlies the drug container 30 when the door 27 is closed. When the hood 28 is closed, with a cassette assembly 32 in place, an open drug identification window 36 is disposed at a forward upper end of the drug channel 12c between the door 27 and the hood 28 to provide scanner access to the drug container 30 and bar code identifying indicia 37 provided on the drug container. Further, the cassette 32a engages a channel door sensor 29a mounted on a wall 29b of drug channel 12c when the door 27 and hood 28 are conjointly closed to provide sensor input to the microprocessor 21. The sensor 29a is not activated and there is no input to the microprocessor 21 when a cassette assembly 32 is not installed in the door 27 and the door 27 and hood 28 are closed.

As seen in FIGS. 4 and 5, the bar code 37 provided on the drug vial 30 is read by a bar code scanner 39 electronically connected to the system 10, as by a cable 39a. Other connections are possible, including a wireless connection. An active reading area 40 is provided at a forward end of the bar code scanner 39. An essential element of the present invention is a magnetic safety latch 41 provided at a forward end of the scanner 39. When the scanner 39 is driven to a position within the drug identification window 36 sufficient to enable the scanner to read the bar code 37 provided on the drug vial 30, a magnet of the latch 41 on the scanner activates a reed switch 43 mounted adjacent window 36 on a fixed arm 44 of the drug channel 12c.

The reed switch 43 is a known device which can be held either normally open or normally closed in the presence of a magnetic device. The switch 43 is activated to a respective closed position by the presence of the magnet in the latch 41, and open when the latch 41 moves away from the switch 43. The closed switch 43 generates a scanner presence signal to the microprocessor 21. When the channel door sensor 29a is activated and the latch 41 activates the reed switch 43, the combined input to the microprocessor 21 activates the scanner 39 to read the bar code 37 on the vial 30 in drug channel 12c.

Drug channel 12c is so configured that drug identification cannot be initiated until a cassette assembly 32 placed in the door 27 activates the door sensor 29a with the closing of the door and hood, and the latch 41 activates the reed switch 43. The system 10 will not display drug type for user confirmation until the drug channel 12c is activated and the drug installed therein is identified by the system. Thus, the drug identification and security apparatus of the present invention will not permit a reading taken from a drug container 30 to be displayed on the touch screen 16c of the drug delivery channel 12c unless the cassette door 28 is closed and the scanner 39 is placed in window 36 to latch the reed switch 43 mounted adjacent the window 36 and generate a scanner presence signal to the microprocessor 21. Moreover, the reed switch 43 is inactivated when the scanner 39 is removed from window 36, to terminate the scanner presence signal and to prevent the scanner from reading a drug container 30 installed in another drug channel or disposed remotely from the system.

Each drug channel 12a, 12b, an 12c has its own reed switch 43 and its own channel door sensor 29a and once a cassette assembly 32 is installed in a drug channel and the door 27 is closed to enable the cassette to activate the door sensor, drug identification can occur in any desired order, i.e., with a respective drug channel door closed, and a cassette assembly 32 in place and with a sensor 29a activated for each of drug channels 12a, 12b and 12c, the bar code scanner 39 can enter the drug channels in any order to enable the scanner's latch 41 to activate the reed switch associated with the selected channel and then read the drug container 30 installed therein.

FIG. 6 shows that both scanner input and channel door sensor input to microprocessor 21 is required to initiate a valid scan process.

As shown in FIGS. 6a and 6b, whenever an activation of cassette position sensor 29a generates a container position signal (such as the Channel ID pattern) or start of a drug container identity data (such as a bar code) is generated by switch 43 in an attempt to identify a drug in a designated position, the relative timing of these two events is compared by the microprocessor 21. Given bar code data starting at time t, the change in Channel ID pattern must occur after a time $t_1$, where $t - t_1 \leq X$. The value X is chosen as an interval too small to allow the repositioning of the bar code scanner outside the designated Channel after the detection of the Channel ID pattern.

When the change in Channel ID pattern occurs after the start of the bar code data, it must occur before a time $t_2$, where $t_2 - t \leq Y$. The value Y is chosen to be an interval too small to allow the repositioning of the bar code scanner outside the designated Channel before the detection of the Channel ID pattern.

If the relative timing between the container position signal and the drug container identity data falls within the boundaries described above, this positively identifies the drug and drug position.

In FIGS. 7 and 8a–8f, the security interlock 24 associated with the drug delivery channel 12c is shown in the full range of motion associated with the opening and closing of the door 27 and the hood 28 conjointly. The interlock 24 comprises a pivotable over-center member 46 that is roughly T-shaped, which rotates around a central pivot point 47. As seen in FIG. 8f, leg 48 of the T-shaped member 46 carries a longitudinal cam track 48a on an inner surface thereof which receives cam follower 50 carried on the door 27.

In the closed position of the lower door 27 (FIG. 8a) cam follower 50 is disposed at an upper end of cam track 48a, and places the member 46 in an over-center position which effectively prevents the door 27 from being opened by direct lateral forces applied to it. In the open position of the door 27 (FIG. 8c) the cam follower 50 is disposed at a lower end of cam 48a.

A sheet spring member 80 mounted on the outside of member 46 conforms generally to a triangular shape and is somewhat larger than member 46 to overlie an outer face thereof. The spring 80 is a stainless steel sheet mounted to member 46 at an inner end by screws 81 and 82. The outer end 80a of spring 80 is bent (FIG. 9) to engage and retain cam follower 50 in track 48 when the door 27 is in the open position of FIG. 8c, but can be moved out of the way to fully rotate door 27 about its lower pivot point 27a, as shown in FIG. 8d, to permit full access to the interior of drug channel 12c for cleaning, repairs, etc. Connecting lever 51 is provided between the lower door 27 and the hood 28. The lever 51 is somewhat S-shaped, with a lower leg 51a pinned at its outer end to the over center member 46 at a pivot point 52. Mid leg portion 51b is integral to the first outer leg 51a at one end and to upper leg portion 51c at its opposite end. Upper leg portion 51c is connected to the hood 28 at pivot point 53. A latch opening 51d is provided at an outer or rear edge of upper leg 51c at a mid-portion thereof and is described in detail below. Hood 28 pivots about a pivot point 54.

Link 56 is pivotally connected to the over center member 46 at pivot point 57. At its opposite end link 56 carries a cam track 58 which both rotates and translates about a pivot point 60 carried on an outer face of side frame 61 of the drug channel 12c. A tension spring 62 is connected at one end to the fixed pivot point 60 and at an opposite end to a fixed point 64 disposed on the member 56 near the mid-point thereof. The spring 62 has a generally semi-circular shape and is under increased tension when the drug channel door 27 is open since the distance between the pins 60 and 64 is reduced with the door opened and the pin 60 at or near the inner end of the track 58.

Because of the over center configuration of the member 46, the cassette door 27 can only be opened by upward movement of the hood 28, with the interconnection of the member 51 between the over-center member 46 and the hood 28 enabling opening both the door and hood as follows.

As the hood 28 is raised, there is some initial movement of the link 51 about its lower pivot point 52 (FIG. 8b). However, because there is no movement of over-center member 46, there is no movement of lower door 27. Once the member 51 is extended to the position of FIG. 8b, further upward movement of the hood 28 causes the member 51 to rotate over-center member 46 about the central pivot 47 and open the lower door 27. Also, link 56 traverses outwardly along its cam track 58 under the force of the upward movement of the hood 28 and against the inward force of spring 62 as the over-center member 46 rotates about its pivot point 47 and the member 51 is translated upward to the open position of the hood 28. At the same time cam follower 50 moves along the cam track 48a in leg 48 to rotate the door outwardly to the open position of FIG. 8c.

Interlock 24 prevents opening of the door 27 and hood 28 of the associated drug channel 12c as follows. A locking member 70 comprises an elongated bale having a closed end 70a, a mid-leg portion 70b, and a hook portion 70c, and which extends the length of drug channels 12a, 12b and 12c. Longitudinal pin 73 extends through the closed end 70a of bale 70 to rest at one end in a bearing 73a disposed in a first frame opening 71 provided in the side frame 61 of the drug channel 12c and at an opposite end in a similar bearing (not shown) disposed in a complementary opening provided an outer side frame (not shown) of the drug channel 12a. The hook portion 70c of bale 70 is biased by a tension spring 75 which is connected at one end to the mid-leg 70b of the bale 70 and at an opposite end to a fixed point 75a provided in the side frame 61 of drug channel 12c. The spring 75 drives the hook portion 70c into latch opening 51d provided in the upper leg 51c of the S-shaped member 51 to latch door 27 and hood 28 in a closed and locked position (FIG. 8a) which prevents movement of member 51 when the bale hook 70c is held in place in the opening 51d by the bias of the tension spring 75.

A rotatable cam 22a (FIGS. 7, 8e) associated with the key lock 22 can be rotated by a key (not shown) inserted into key lock 22. The cam 22a engages the flat mid-leg portion 70b of the bale 70 to move and hold the bale hook portion 70c at a position out of engagement with the latch opening 51d in the connecting member 51 and against the bias of the spring 75 to permit upward movement of the member 51 to open the hood 28 and the door 27 of the drug channel 12c.

When the bale 70 is biased to a lock position by the springs 75 of the drug channels 12a, 12b, 12c and the cam 22a, and the hood 28 of one or more drug channels is raised, any closed drug channel can be reopened because the bale hook 70c is co-extensive with the pin 73 across all drug channels and the member 51 associated with the raised hood 28 is translated upwardly to place a flat rear or outer edge of leg portion 51c below the latch opening 51d into engagement with the hook 70c and bias hook 70c out of engagement with latch portions 51d of members 51 of other drug channels. When the hook 70c is biased out of engagement with one latch opening 51d as described above, the hook is biased out of engagement with latch openings 51d associated with the closed drug channels, and they can be reopened, i.e., if the bale hook 70c is disengaged from the latch opening 51d of any drug channel, all drug channels can be reopened until the last drug channel is closed. This is true even though hook 70c is not biased as far outwardly from the latchopenings 51d as when the cam 22a is activated to move the hook 70c out of latches 51d. Thus, if a drug channel is open, any closed drug channels can be reopened by upward movement of their respective hood 28. Once all the drug channels are closed, the bale 70 is biased into all latches 51d and all the drug channels 12a, 12b and 12c are closed and cannot be reopened without the use of the key lock 22 and associated cam 22a. The key lock 22 must rotate its associated cam 22a against the bale 70 and against the bias of the spring 75 to rotate the hook 70c out of the latch opening 51d of the lever 51 to enable the interaction of hood 28, door 27, lever 51, and the over-center member 46 to open the door and hood of all drug channels.

A secondary feature of the interlock 45 is the interaction of the bale 70 with a microswitch 76. An actuating arm 76a of the microswitch 76 is disengaged when the bale 70 is biased into a locking position by the spring 75. In the locking position, the bale 70 is biased away from the arm 76a and the microswitch 76 is normally open, to direct a signal to the microprocessor 21 which the microprocessor interprets as a signal to interrupt drug flow from the system to the patient. When the bale 70 is biased to an unlocked position, it engages arm 76a to close microswitch 76 to direct a signal to the microprocessor 21, which the microprocessor interprets as a signal to resume drug flow from the system to the patient.

Thus, a user can install a drug vial 30 in a respective drug delivery channel 12a, 12b or 12c, program each channel of the drug delivery apparatus 10 and lock up the apparatus through the key lock 22 which causes the bale 70 to engage the levers 51 to lock the door 27 and the hood 28 closed and also to interrupt drug flow from the system 10 to the patient through the micro switch 76 which is normally open when the bale engages the levers 51.

When the bale 70 is released, the bale engages the micro switch 76 to a closed position which activates the drug delivery apparatus 10 to enable the attending physician to begin the infusion of the patient through one or more programmed drug delivery channels 12a, 12b, 12c of the system 10. As noted above, the drug channel 12c is not automatically locked when its hood 28 is open and the bale 70 is turned to a lock position. The attending physician can turn the bale 70 to a lock position and then complete his installation of a drug vial 30 in the open drug delivery channel 12c. When the bale 70 is in the lock position, if one or more hoods 28 are in the open position, all closed hoods 28 are not locked. Note, however that a known bale, more complex than bale 70, would enable independent locking of drug channels 12a, 12b and 12c. Note also that the normally open/normally closed dichotomy for the microswitch 76 is the configuration for the preferred embodiment and the alternative configuration is possible.

Note also that there is no interconnection between scanner interlock 41 and hood interlock 24. The attending physician may simply lock each drug vial 30 in its respective drug delivery channel 12a, 12b or 12c and scan each drug vial to program the apparatus 10 just prior to infusing the patient.

Thus, the present drug identification and security apparatus provides multiple safeguards for both the patient and the attending physician to ensure that the drug container is properly installed in the device and to insure that the device can be easily electronically disengaged by the attending physician when he moves away from the apparatus. A further desirable feature of the present invention is that the drug container is locked in the drug delivery system 10 when the system is disengaged, to prevent removal of the drug container from the system when the attending physician is not present.

Having described the preferred embodiment of the invention, it is believed that the specific description set forth herein should not be limiting, but rather that the present invention shall be limited by the claims appended hereto.

We claim:

1. An electronic drug delivery system comprising at least one pump mechanism having upper and lower doors, a pump cassette assembly disposable in said pump mechanism, said upper and lower doors to open to enable installation of the cassette assembly therein, and a drug identification and security apparatus usable with said drug delivery system, said apparatus including:
   a pivotable structure operatively disposed between the upper and lower doors to effect conjoint opening and closing thereof;
   a latching portion provided in the pivotable structure;
   a pivotable locking bale, movable between a lock position in which the upper and lower doors are closed and the bale engages the latching portion of the pivotable structure to hold the doors closed, and an unlock position, in which the bale disengages the latching portion of the pivotable structure to enable opening of the doors;
   an interrupt mechanism electronically connected to the pump mechanism and interposed between the locking bale and the pump mechanism to selectively interrupt operation of the pump mechanism when the bale moved from the lock to the unlock position; and
   a key lock associated with the pivotable bale to move said bale between said lock and unlock positions.

2. An electronic drug delivery system as claimed in claim 1 wherein the interrupt mechanism includes a normally open micro-switch connected to the drug delivery system which is closed when the locking bale engages the micro-switch in an unlock position for the locking bale to operate the system and normally open when the locking bale engages the pivotable structure in a lock position of the bale to interrupt the system.

3. An electronic drug delivery system as claimed in claim 1, wherein the upper door of the pump mechanism comprises an enclosing hood for the drug container, said upper door and hood having disposed at a conjoint forward portion thereof an open drug identification window.

4. An electronic drug delivery system as claimed in claim 3 wherein the apparatus includes a reading device electronically connected to the system for reading identifying indicia on the drug container installed in the pump mechanism; and an interlock interposed between the reading device and the pump mechanism to initiate a scan of the drug container installed in the pump mechanism, the interlock including:
   a cassette presence sensor provided in the pump mechanism to engage a cassette assembly held in the closed door of the mechanism;
   a sensor disposed in the reading device and a sensing device fixedly mounted in the pump mechanism adjacent the drug identification window thereof, a drug container of a cassette assembly mounted in the pump mechanism, and having identifying indicia provided thereon, said indicia displayed in said drug identification window, and controlling means structure in the system to receive inputs from the sensors, initiate the reading, and receive information from the reading device, whereby engagement of the sensor in the reading device with the sensing device in the pump mechanism activates the reading device to read the identifying indicia on the drug container and transmit information coded thereon to the drug delivery system, when the cassette presence sensor is activated in conjunction therewith.

5. An electronic drug delivery system as claimed in claim 4 wherein the reading device is a bar code reader and the identifying indicia provided on the drug container is a specific bar code identifier for the drug within the container.

6. A drug delivery system, said system comprising a plurality of drug delivery channels, each of which comprises a pump mechanism having upper and lower doors, a pump cassette assembly disposable in each of said pump mechanisms, said upper and lower doors to open to enable installation of a pump cassette assembly therein, and a drug identification and security apparatus usable with said drug delivery system, said apparatus including:
   a pivotable structure operatively disposed between the upper and lower doors to effect conjoint opening and closing thereof;
   a latching portion provided in the pivotable structure;
   a pivotable locking bale, movable between a lock position in which the upper and lower doors are closed and the bale engages the latching portion of the pivotable structure to hold the doors closed and an unlock position, in which the bale disengages from the latching portion of the pivotable structure to enable opening of the doors;
   an interrupt mechanism electronically connected to the pumping mechanism and interposed between the locking bale and the drug delivery apparatus to selectively interrupt operation of the pump mechanism when the bale moves from, the lock to the unlock position; and
   a key lock associated with the pivotable bale to move said bale between said lock and unlock positions.

7. An electronic drug delivery system as claimed in claim 6 wherein the interrupt mechanism includes a normally open micro-switch connected to the drug delivery system, which is closed when the locking bale engages the micro-switch in an unlock position for the locking bale to operate the system and normally open when the locking bale engages the pivotable structure in a lock position of the bale to interrupt the system.

8. An electronic drug delivery system as claimed in claim 6, wherein the upper door of the pump mechanism comprises an enclosing hood for the drug vial, said upper door and hood having disposed at a conjoint forward portion thereof an open drug identification window.

9. An electronic drug delivery system as claimed in claim 8 wherein the system includes a reading device electronically connected to the system for reading identifying indicia provided on the drug container installed in the pump mechanism, said apparatus including an interlock mechanism interposed between the reading device and each drug channel to assure the placement of the cassette assembly including the drug container in the appropriate drug channel at the drug identification window, the interlock including:

a cassette presence sensor provided in each pump mechanism to engage a cassette assembly held in the closed door of the mechanism;

a sensor disposed in the reading device, and a sensing device fixedly mounted in each drug channel adjacent the drug identification window thereof, a drug container of a cassette assembly mounted in each drug channel of the drug delivery system, and having identifying indicia provided thereon, said indicia displayed in said window, and controlling means structure in the system to receive inputs from the sensors, initiate the reading, and receive information from the reading device, whereby engagement of the sensor in the reading device with the sensing device in the drug channel activates the reading device to read the identifying indicia on the drug container and transmit information coded thereon to the drug delivery system, when the cassette presence sensor is activated in conjunction therewith.

10. An electronic drug delivery system as claimed in claim 9 wherein the reading device is a bar code reader and the identifying indicia provided on the drug container is a specific bar code identifier for the drug within the container.

11. A electronic drug delivery system, said system comprising at least one pump mechanism having a pump cassette assembly therein, a drug container provided in the cassette assembly, said container having identifying indicia thereon, said drug identification and security apparatus including:

a reading device interconnected with the system, said reading device having sensors for reading an identifying indicia provided on the drug container, said system including a controlling means to interact with the reading device and its sensors;

and an interlock interposed between the reading device and the pump mechanism including a cassette presence sensor in the mechanism, an activating magnet on the reading device and a switch fixedly mounted on the mechanism, said sensor to be activated by the presence of a cassette in the mechanism and said switch to be activated by the proximity of the magnet on the reading device, to enable the apparatus to read the identifying indicia on the drug container.

12. An electronic drug delivery system comprising at least one pump mechanism having a pump cassette assembly therein, and a drug container provided in the cassette assembly, and a security apparatus including:

upper and lower doors of the pump mechanism, said upper and lower doors selectively held closed and opened by a pivotal structure interconnected therewith, said open doors to permit installation and removal of a drug container within the pump mechanism disposed in the system, a latching portion provided on the pivotal structure, a locking bale pivotally mounted on the pump mechanism for engagement with the latching portion of the pivotal structure and movable between a lock position in engagement with the latching portion of the pivotal structure and an unlock position disengaged with respect to said latching portion; and a normally open position sensor electronically connected to the system which is disengaged to electronically interrupt the drug delivery system when the locking bale moves out of engagement with the sensor and into engagement with the latching portion of the pivotal structure in a lock position therefor.

13. An electronic drug delivery system, said system including a security apparatus comprising:

a cassette assembly holding compartment having pivotal upper and lower outer doors to open and close said compartment;

a door operating structure for selectivally preventing and enabling opening of said upper and lower doors, said door operating structure including an over-center apparatus engaging the lower door;

a connecting link between the upper door and the over-center apparatus of the lower door;

a latching member pivotally mounted on said compartment;

biasing means for biasing the latching member into latching engagement with said connecting link; and a cam arrangement interconnected to said latching member and operable against the bias of the latching member to disengage said member from said connecting link, whereby disengagement of the latching member from the connecting link by the cam arrangement selectively prevents and enables opening of said upper and lower doors by the movement of the door operating structure through the link connected to the upper door, and said over-center apparatus includes further biasing means operable to retain the lower door closed against lateral forces directed at the lower door only.

14. An electronic drug delivery system as claimed in claim 13 wherein a switch is interposed between a frame member of the cassette holding compartment and the latching member, said switch normally open to electronically interrupt the electronic drug delivery system when the latching member is biased into latching engagement with said connecting link, and said switch engaged by the latching member when the latching member is disengaged from the connecting link so as to electronically operate the electronic drug delivery system.

15. An electronic drug delivery system as claimed in claim 14 wherein said electronic drug delivery system includes a microprocessor and a first input from the switch to the microprocessor will electronically disable the microprocessor when the latching member associated with the door operating structure is biased into latching engagement with said connecting link and a second input from the switch to the microprocessor will electronically activate the microprocessor when the latching member is disengaged from the connecting link.

16. An electronic drug delivery system as claimed in claim 13 wherein said apparatus includes a reading device interconnected to the system to read identifying indicia provided on a drug container associated with a cassette assembly installed in the cassette holding compartment of the drug delivery system and an interlock switch disposed in said compartment and interconnected between the reading device and the system which prevents the reading device from reading the identifying indicia provided on the drug container unless the cassette assembly is inserted in the cassette holding compartment and the upper and lower doors of said cassette holding compartment are closed.

17. An electronic drug delivery system as claimed in claim 16 wherein the interlock includes a cassette presence sensor which is activated when the cassette assembly is inserted in the cassette holding compartment and the upper and lower outer doors of the compartment are closed to hold the cassette assembly in an operating position within the compartment, an open window between the upper and lower doors of the compartment to admit a reading device associated with the system, a switch disposed in the lower door of the compartment adjacent the window, and a device sensor disposed in the reading device, whereby the cassette presence sensor and the door switch are cooperatively interactive when a cassette is held in the compartment in an operating position of the electronic drug delivery system, controlling means structure in the system to receive inputs from the sensors, initiate the reading, and receive information from the reading device, and activation of the cassette presence sensor enables activation of the door switch by the device sensor to enable reading of the indicia on the drug container received in the cassette assembly holding compartment.

18. An electronic drug delivery system as claimed in claim 13 wherein the over-center apparatus is mounted on a frame of of said compartment and includes a pivotal over-center member carrying an elongated cam track on one side thereof, said cam track receiving a cam follower of the lower door, said cam follower mounted on the lower door to traverse the cam track between an open and closed position of the lower door.

19. An electronic drug delivery system as claimed in claim 18 wherein a lower end of the cam track provided on the over-center member is open and a flat stainless steel spring is mounted on a flat outer face of the over-center member, said stainless steel spring bent to close at an outer end of the cam track to hold the cam follower of the lower door within the cam track and movable away from the over-center member to permit the cam follower to be released therefrom to permit the lower door to fully pivot around a lower pivot point thereof.

20. An electronic drug delivery system as claimed in claim 19 wherein the over-center apparatus includes a slidable link pivotally mounted to the over-center member at one end and a cam track engaging a fixedly mounted point on the frame of the said compartment at an opposite end.

21. An electronic drug delivery system as claimed in claim 20 wherein the slidable link includes a tension spring mounted between the fixed mounted point and a second point generally located at a mid-portion of the link, the spring operative to assist in driving the over-center member around a central pivot point thereof to a over-center position in which the lower door of the cassette holding compartment is fully closed.

22. An electronic drug delivery system as claimed in claim 21 wherein the connecting link is a generally S-shaped link which has a bottom end pivotally connected to the over-center member and an upper end pivotally mounted to the upper door of the cassette holding compartment, whereby pivoting of the upper door to an open position pivots the upper connecting point upward to translate the S-shaped link upward and pivot the over-center member about its central pivot point and selectively prevents and enables opening of the lower door.

23. An electronic drug delivery system as claimed in claim 22 wherein the S-shaped link includes an upper leg portion having a latch receiving notch therein.

24. An electronic drug delivery system as claimed in claim 23 wherein the latching member comprises a latching bale rotatably mounted in opposite side walls of said compartment, the latching bale including a closed lower portion engaging a pin about which the bale rotates, a mid leg portion, an upper hook portion and a biasing spring which in a latching position of the latching bale biases said hook portion into the latching notch of the S-shaped member of the door operating structure.

25. An electronic drug delivery system as claimed in claim 24 wherein a key lock includes an associated cam, said cam engaging the latching bale and movable to a first position which enables the latching bale to engage the latching notch of said S-shaped member of the door operating structure in a locking position which holds the upper and lower door closed, said cam movable to a second position to move the latching bale out of engagement with the notch of the S-shaped link to enable said upper and lower doors to be opened.

26. An electronic drug delivery system including drug identification and security apparatus comprising:
 a cassette holding compartment having pivotal upper and lower outer doors to open and close said compartment;
 a door operating structure for simultaneously opening and closing said upper and lower doors, said door operating structure including an over-center apparatus engaging the lower door;
 a connecting link between the upper door and the over-center apparatus;
 a latching member pivotally mounted on said compartment;
 biasing means for biasing the latching member into latching engagement with said connecting link;
 a cam arrangement interconnected to said latching member and operable against the bias of latching member to disengage said member from said connecting link;
 a cassette presence sensor disposed in the cassette holding compartment and operative when a cassette assembly is installed in the cassette holding compartment and the upper and lower doors are closed to hold the cassette assembly within the cassette holding compartment;
 a scanning window disposed in the compartment between the upper and lower doors to provide access to scanning indicia disposed on a drug container of the cassette assembly;
 a scanner electronically connected to the electronic drug delivery system and operative to read the identifying indicia provided on the drug container installed in the cassette holding compartment;
 a switch disposed in the lower door of the cassette holding compartment and adjacent the scanning window of the compartment;
 a sensor disposed on the scanner so as to be placed in close proximity to the switch on the lower door of the cassette holding compartment when the scanner is disposed adjacent the scanning window of the compartment; and controlling means structure in the system to receive inputs from the sensors, initiate the reading, and receive information from the reading device, whereby the cam arrangement moves the latching member out of engagement with the connecting link enabling said upper and lower doors to be opened by the movement of the door operating structure through the connecting link, and said over-center apparatus includes further biasing means operable to retain the lower door closing against lateral force is directed at the lower door only and, when the upper and lower doors are closed, the scanner sensor is operative to read the identifying indicia provided on the drug container in the cassette assembly holding compartment when the cassette sensor switch in the compartment is activated therewith.

27. An electronic drug delivery system including drug identification and security apparatus comprising:
   a cassette holding compartment having pivotal upper and lower outer doors to open and close said compartment;
   a scanning window disposed in said cassette holding compartment at a conjoint forward position of said closed upper and lower doors;
   a cassette presence sensor provided in said compartment and operative when a cassette assembly is installed in said compartment and the upper and lower doors are closed;
   a switch disposed in one of the doors of the compartment and adjacent the scanning window thereof;
   a scanning device electronically connected to the drug delivery system and operable to be inserted into the scanning window of the cassette holding compartment;
   a sensor so positioned on the scanning device as to be brought in close proximity to the switch on the cassette holding compartment when the scanning device is inserted into the scanning window of the compartment; and controlling means structure in the system to receive inputs from the sensors, initiate the reading, and receive information from the reading device, whereby activation of the cassette presence sensor will enable activation of the switch provided in the scanning window to enable the scanning device to read identifying indicia provided on a drug container of a cassette assembly, said drug container disposed at the scanning window of the cassette holding compartment.

28. An electronic drug delivery system including drug identification and security apparatus comprising:
   a holding compartment having open and closed positions;
   an operating structure opening and closing said compartment;
   a container presence sensor disposed in the holding compartment and operative when a drug container is installed in the holding compartment and the compartment is closed to hold the drug container therein;
   a scanner access to provide access to identifying indicia disposed on a drug container installed in the compartment;
   a scanning device electronically connected to the electronic drug delivery system and operative to read the identifying indicia provided on the drug container installed in the compartment;
   a switch disposed adjacent the scanner access of the compartment;
   a sensor disposed on the scanning device so as to be placed in close proximity to the switch on the holding compartment when the scanning device is inserted into the scanner access of the compartment and controlling means structure in the system to receive inputs from the sensors, initiate the reading, and receive information from the reading device;
   whereby, when the compartment is closed the scanner sensor is activated by said controlling means structure in the system to read the identifying indicia provided on the container in the holding compartment when the container presence sensor in the compartment is activated therewith, in a time sequence which prevents the scanner from operating on a drug container not installed in the compartment.

29. An electronic drug delivery system including a drug identification and security apparatus comprising:
   a holding compartment;
   a scanner access disposed in said holding compartment;
   a container presence sensor provided in said compartment and operative when a drug container is installed in said compartment;
   a switch disposed on said compartment;
   a scanning device electronically connected to the drug delivery system and operable to be inserted into the scanner access of the holding compartment;
   a scanning sensor so positioned on the scanning device as to be brought in close proximity to the switch on the holding compartment when the scanner is inserted into the scanner access; and controlling means structure in the system to receive inputs from the sensors, initiate the reading, and receive information from the reading device whereby activation of the container presence sensor will enable activation of the switch provided on the scanning device to enable the scanner to read identifying indicia provided on the drug container and disposed at the scanner access of the holding compartment.

30. An electronic drug delivery system including a drug identification and security apparatus comprising:
   a holding compartment;
   a scanner access disposed in said holding compartment;
   a container presence sensor provided in said compartment and operative when a drug container is installed in said compartment;
   a scanning device electronically connected to the drug delivery system; and
   controlling means structure in the system to receive inputs from the sensors, initiate the reading, and receive information from the reading device; whereby activation of the container presence sensor will enable scanner access to enable the scanning device to read identifying indicia provided on the drug container and disposed at the scanner access of the holding compartment.

* * * * *